(12) United States Patent
Vidal et al.

(10) Patent No.: US 11,253,172 B2
(45) Date of Patent: Feb. 22, 2022

(54) LOCOGRAM SOFTWARE: TOOL FOR ANALYSING GAIT EXERCISES

(71) Applicants: UNIVERSITE PARIS DESCARTES, Paris (FR); CENTRE NATIONAL DE LA RECHERCHE SCIENTIFIQUE, Paris (FR); UNIVERSITE PARIS NORD, Villetaneuse (FR); ETAT FRANCAIS—MINISTERE DE LA DEFENSE—DIRECTION CENTRALE DU SERVICE DE SANTE DES ARMEES, Paris (FR)

(72) Inventors: Pierre Vidal, Paris (FR); Rémi Barrois-Muller, Paris (FR); Damien Ricard, Clamart (FR); Laurent Oudre, Paris (FR)

(73) Assignees: UNIVERSITE DE PARIS, Paris (FR); CENTRE NATIONAL DE LA RECHERCHE SCIENTIFIQUE, Paris (FR); UNIVERSITE PARIS NORD, Villetaneuse (FR); ETAT FRANCAIS—MINISTERE DE LA DEFENSE—DIRECTION CENTRALE DU SERVICE DE SANTE DES ARMEES, Paris (FR)

( * ) Notice: Subject to any disclaimer, the term of this patent is extended or adjusted under 35 U.S.C. 154(b) by 143 days.

(21) Appl. No.: 16/476,484

(22) PCT Filed: Jan. 9, 2018

(86) PCT No.: PCT/EP2018/050450
§ 371 (c)(1),
(2) Date: Jul. 8, 2019

(87) PCT Pub. No.: WO2018/130521
PCT Pub. Date: Jul. 19, 2018

(65) Prior Publication Data
US 2019/0380623 A1    Dec. 19, 2019

(30) Foreign Application Priority Data

Jan. 10, 2017 (FR) .................................. 1770031

(51) Int. Cl.
*A61B 5/11* (2006.01)
*A61B 5/00* (2006.01)
*A61B 5/389* (2021.01)

(52) U.S. Cl.
CPC ............ *A61B 5/112* (2013.01); *A61B 5/1123* (2013.01); *A61B 5/389* (2021.01); *A61B 5/7246* (2013.01);

(Continued)

(58) Field of Classification Search
CPC ......... A61B 5/112; A61B 5/389; A61B 5/223; A61B 5/7346; A61B 5/743; A61B 5/6829;

(Continued)

(56) References Cited

U.S. PATENT DOCUMENTS

2019/0150793 A1* 5/2019 Barth .................... A61B 5/7267

OTHER PUBLICATIONS

Yang, Mingjing, et al. "iGAIT: an interactive accelerometer based gait analysis system." Computer methods and programs in biomedicine 108.2 (2012): 715-723. (Year: 2012).*

(Continued)

*Primary Examiner* — Sean P Dougherty
*Assistant Examiner* — Alexander H Connor
(74) *Attorney, Agent, or Firm* — Steven M. Shape; Dennemeyer & Associates, LLC

(57) ABSTRACT

A device for analyzing the regularity and symmetry of a sequence of N gait or running cycles of a person, comprising sensors for measuring raw time signals of a physical movement variable of a body segment, a processing unit connected to the sensors for measuring and configured to (Continued)

separate the raw time signals into distinct time signals $C_i$, the $C_i$ series being associated with a given gait or running cycle $i$ of the person, to calculate at least one similarity coefficient between the signal $C_i$ associated with gait or running cycle $i$ and another signal $C_j$ associated with a gait or running cycle $j$ of the person. A display is configured to display the matrix $M(i,j)$ with each value of the similarity coefficient shown in the matrix $M(i,j)$ in color to form a graduated color scale indicating the similarity between the gait or running cycles $i$ and $j$.

20 Claims, 8 Drawing Sheets

(52) U.S. Cl.
CPC ...... *A61B 5/743* (2013.01); *A61B 2562/0219* (2013.01); *A61B 2562/0247* (2013.01)
(58) Field of Classification Search
CPC .......... A61B 5/4082; A61B 2562/0219; A61B 2562/0247; G01C 22/006
See application file for complete search history.

(56) References Cited

OTHER PUBLICATIONS

European Patent Office, International Search Report, dated May 16, 2018, World Intellectual Property Organization, Rijswijk.
Yang Mingjing et al, "iGAIT: An interactive accelerometer based gait analysis system", Computer Methods and Programs in Biomedicine, vol. 108, No. 2, 2012, pp. 715-723, XP028974078, ISSN: 0169-2607, DOI: 10.1016/J.CMPB.2012.04.004, abstract sections 1, 2.2.3, 2.2.7.
Moe-Nilssen R et al, "Estimation of gait cycle characteristics by trunk accelerometry", Journal of Biomechanics, Pergamon Press, New York, NY, US, vol. 37, No. 1, 2004, pp. 121-126, XP004895603, ISSN: 0021-9290, DOI: 10.1016/S0021-9290 (03) 00233-1 titre, abrege, section 2.1.1.
Che-Chang Yang et al, "Real-Time Gait Cycle Parameter Recognition Using a Wearable Accelerometry System", Sensors, vol. 11, No. 12, Jul. 25, 2011 (Jul. 25, 2011), pp. 7314-7326, XP055364449, DOI: 10.3390/s110807314 sections 1, 2.1, 2.3.

* cited by examiner

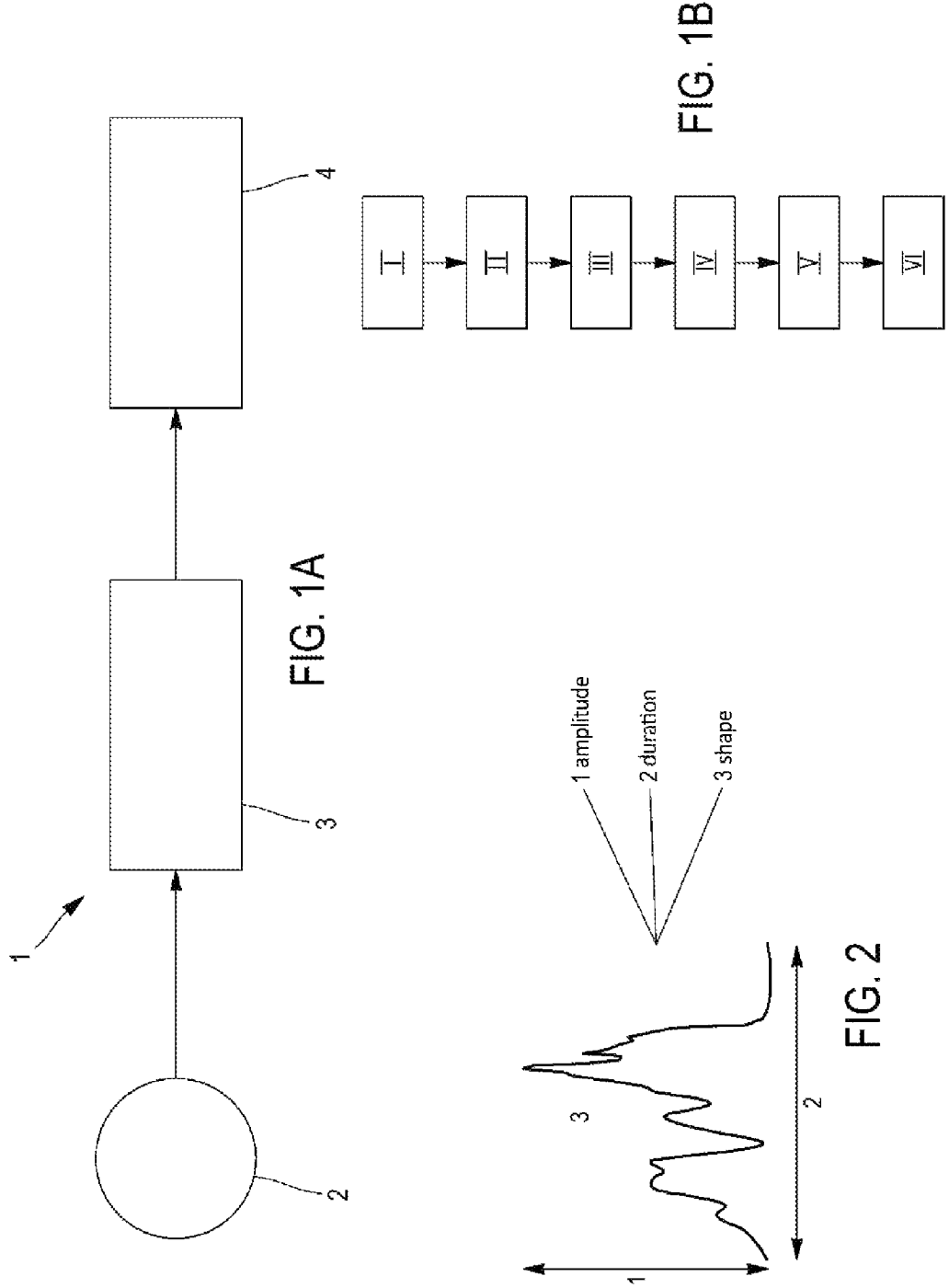

LOCOGRAM SOFTWARE: TOOL FOR ANALYSING GAIT EXERCISES

CROSS-REFERENCE TO RELATED APPLICATIONS

This is a 35 U.S.C. 371 National Stage Patent Application of International Application No. PCT/EP2018/050450, filed Jan. 9, 2018, which claims priority to French application 1770031, filed Jan. 10, 2017, each of which is hereby incorporated by reference in its entirety.

FIELD OF THE INVENTION

The present invention concerns a device for analysing the regularity and symmetry of a sequence of an individual's gait or running cycles.

PRIOR ART

Recently, advances in electronics and informatics have led to the development of new sensors which make it possible to measure the gait within a routine clinical consultation (for example using inertial sensors). These sensors give access to signals which need to be summarised for conclusions to be drawn about an individual's gait.

Gait parameters such as speed or cadence are the most summarised form of gait signals, as they reduce the signals to a number. Thus, the manufacturers of tools for measuring steps provide exhaustive reports in the form of lists of parameters expressing the various aspects of an individual's gait, such as symmetry, regularity or swiftness of start.

There may be more than a hundred parameters. They are presented in a suitable way in the form of a table, bar chart or curve.

Nevertheless, the subject of viewing the intermediate data between the uninterpretable raw time signals and the parameters has not been investigated to any great extent.

In order to be calculated, some parameters require thresholds to be defined. Thus, for example, it is defined that an individual has reached an established rhythm when the amplitude of their cycles has exceeded 67% of the amplitude of cycles 5 to 10 (it is no longer considered accurate to refer to the 'beginning' at more than five cycles). Some cycles may have limit values (60% or 70% of the amplitude of the remote cycles).

In this way, errors occur in connection with the chosen threshold, which could be avoided by directly considering the raw data.

The parameters average out the gait characteristics over the whole exercise, and because of this they mask the progress of the exercise. For example, to evaluate the regularity of an individual's gait, the standard deviation of the duration of the gait cycles is used. If the cycles are regular overall and one cycle is found to be longer than the others, the standard deviation will be increased. It will not be known that this increase is due to an isolated cycle, or at what point in the walk this occurred. The number of erratic cycles and the time of their occurrence are important analytical information.

The parameters are good indicators of an individual's walking performance. However, they do not provide analytical information on the origin of the change in the gait. For example, the speed of walking is a good overall evaluation, but a speed may be reduced by shorter steps or a reduced cadence. The size of the steps and the cadence can in turn be affected by various factors.

Measurement of walking shows major inter-individual fluctuations due mainly to anatomical and functional variations in each individual, which influence the positioning of the sensors, and to variability of locomotion style in each individual. The parameters are affected by this variability and no reference method exists for eliminating it.

DISCLOSURE OF THE INVENTION

A need exists in the prior art for a method for investigating the regularity and symmetry of a sequence of an individual's gait or running cycles over time.

One object of the invention is to make it possible to take into account the shape of the signal to report on the regularity of the gait or running, while eliminating the variability of the duration or amplitude of the gait or running cycles.

In the invention, a visualisation matrix or table of a gait or running exercise is designed. This visualisation matrix $M(i,j)$ is called a 'locogram' and is a Gramian matrix in which $xij=xij$, with $xij$ being the value in row i and column j in the matrix $M(i,j)$.

The locogram is robust in respect of the type of sensors used (accelerometers, gyroscope, infra-red tracker), as well as in respect of their anatomical sites for the recording of the walk (foot, leg, waist, wrist, head).

Owing to the visualisation matrix according to the invention, the professional who analyses the gait (doctor, physiotherapist, nurse, podiatrist, coach, sports trainer, shoe designer, etc.) can have a global view of the gait exercise, on the basis of which they can do the semiology to get an idea of the quality of the patient's gait and easily spot an exercise with atypical steps. The parameters alone are not enough to get a satisfactory snapshot of the patient. The visualisation matrix is a midway point between the parameters and the raw time signals, and gives the doctor access to the patient's gait data.

The visualisation matrix is based on the division of the gait or run into cycles. The cycles are compared with each other using mathematical 'distances' or metrics. Depending on the choice of distance, a particular aspect of the signal will be compared.

To be more precise, the invention provides a device for analysing the regularity and symmetry of a sequence of N cycles of an individual's gait or run over time by means of a visual representation, the cycles being compared with each other, and for determining the presence and number of erratic cycles as well as the number of cycles necessary to establish walking or running rhythms, and at what point these erratic walking cycles and rhythms are reached, comprising:

measurement sensors for raw signals that are inertial and/or relate to a physical movement variable of at least one body segment; the body segment may, for example, be one or both feet, arms or wrists, or the head, the abdominal waist; the raw signals may, for example, be inertial data;

a processing unit connected to the measurement sensors to:

process and separate the raw time signals into distinct time signals Ci, each time signal Ci being a temporal series of points of the measured physical variable and having a given shape, amplitude and duration, the series Ci being associated with a given cycle i of the individual's gait or run;

calculate at least one similarity coefficient $x_{ij}$ between the signal Ci associated with the cycle i and another signal Cj associated with a cycle j of the same individual, the similarity coefficient xij being: a similarity coefficient of the shape (fij) of the two signals Ci and Cj, a similarity coefficient of the amplitude (aij) of the two signals Ci and Cj, or a similarity coefficient of the duration (dij) of the two signals Ci and Cj, order the value of the similarity coefficient xij (fij, aij, dij) in a square matrix M(i,j) [F(i,j), A(i,j) D(i,j)], in each cell (i,j) in row i and in column j;

where i and j are natural integers ranging from 1 to N, the N gait cycles investigated being in chronological order, according to their order in the gait or running sequence;

display means linked to the processing unit and displaying the square matrix M(i,j) [F(i,j), A(i,j) D(i,j)] with each similarity coefficient value xij (fij, aij, dij) represented in the matrix M(i,j) [F(i,j), A(i,j) D(i,j)] by a graduated visual representation, this value being within an interval between two extreme values, continuously, without thresholds, to make it possible to visually and simultaneously determine:

the similarity between all the gait and running cycles i and j of the same person, each cycle being compared with the others, the number of erratic cycles and the number of cycles necessary to establish gait or running rhythms, and at what point in the sequence these erratic cycles and rhythms are reached.

The locomotion approach using the visualisation matrix suggests describing a cycle (walking, running, marching on the spot) according to three aspects (cycle duration, amplitude and shape) about which similarity distance calculations will be performed. The amplitude and the shape of the signal are independent aspects.

Advantageously, to describe an individual's steps (walking, running, marching on the spot), it may be useful to design three visualisation matrices F(i,j), A(i,j), D(i,j) using these three distances.

The present invention also concerns a method using the device defined above, comprising, as steps:

a detection step (i) for detecting raw time signals of a physical movement variable of at least one body segment, measured in a sequence of N gait or running cycles i of the person, a processing and separation step (ii) for processing and separating the raw time signals into distinct time signals Ci, each time signal Ci being a series of points of the measured physical variable and having a given shape, amplitude and duration, the series Ci being associated with a given gait or running cycle i of the person;

a calculation step (iii) for calculating at least one similarity coefficient xij (fij, aij, dij) between a signal Ci associated with the gait or running cycle i and another signal Cj associated with a gait or running cycle j, representing the similarity between the two signals Ci and Cj;

the coefficient being: a similarity coefficient of the shape fij of the two signals Ci and Cj, a similarity coefficient of the amplitude aij of the two signals Ci and Cj, or a similarity coefficient of the duration dij of the two signals Ci and Cj;

an ordering step (iv) for ordering the value of the similarity coefficient xij in a square matrix M(i,j) in row i and in column j;

where i and j are natural integers ranging from 1 to N, the N gait or running cycles being in chronological order;

a display step (v) for displaying the square matrix M(i,j), each similarity coefficient value xij being represented in the matrix M(i,j) by a graduated visual representation to make it possible for the similarity between the investigated cycles i and j of walking, running or marching on the spot to be seen with the naked eye.

DESCRIPTION OF THE FIGURES

Other goals, features and advantages will become clear from the following detailed description with reference to the drawings, which are provided as an illustrative, non-limiting example and in which:

FIG. 1a shows the device according to the invention;

FIG. 1b shows the method according to the invention;

FIG. 2 shows the definition of terms amplitude, duration and shape of the gait or running cycles;

Figure 3:
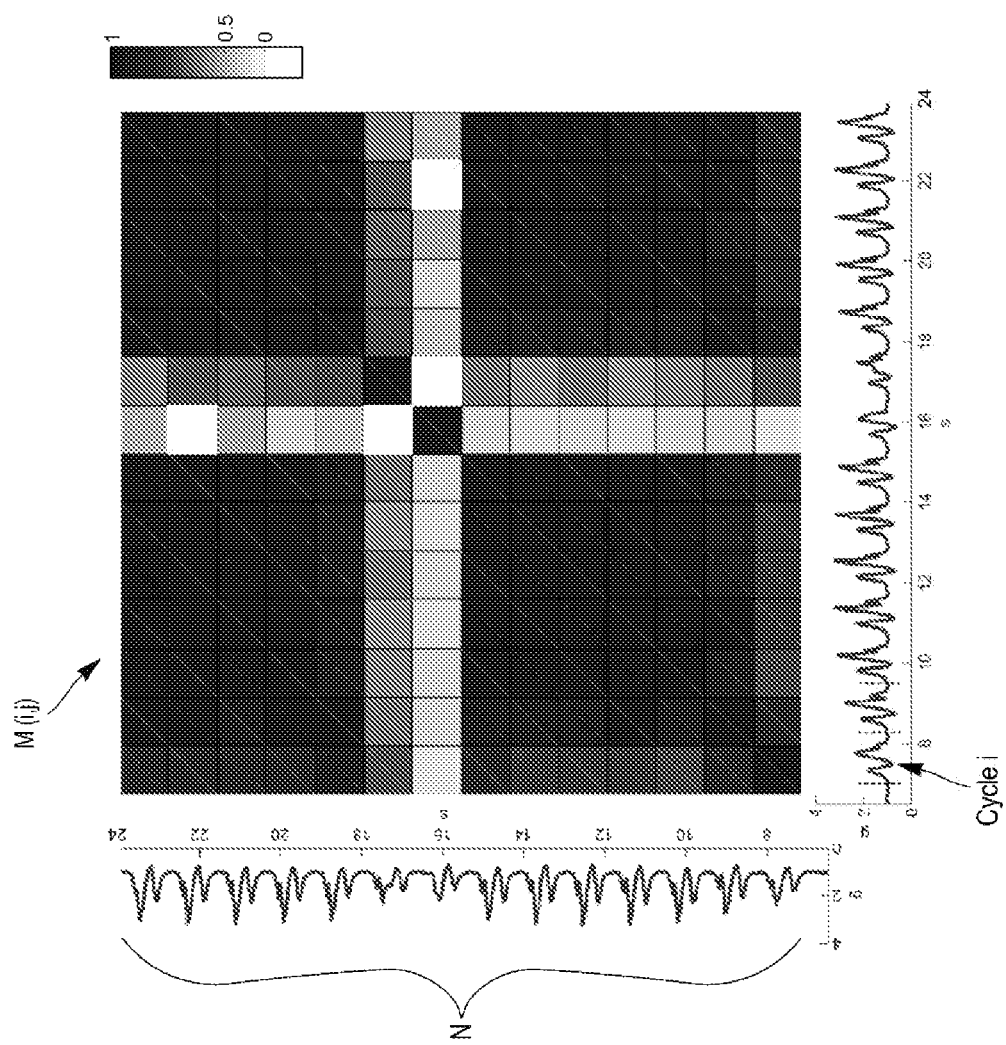
FIG. 3 shows the tool according to the invention for viewing the gait cycle of one foot of a person in a given gait exercise involving walking a defined distance 'there and back'.

The figures presented in this document are only for the purpose of illustration.

DETAILED DESCRIPTION OF THE INVENTION

The present invention concerns a device 1 for analysing the regularity and symmetry of a sequence of N gait or running cycles of an individual over time, without calculation of parameters based on the overall consideration of the N gait or running cycles, by comparing each cycle with each of the other cycles.

The term 'gait or running cycle' corresponds to the defined phases between two heel strikes of the same foot on the ground during the individual's walk or run which took place at certain moments between the two heel strikes. It is therefore representative of the behaviour of the person's foot during a step.

As is known from the prior art, different phases can be defined as percentages, 0% corresponding to the first heel strike and 100% to the second.

The cycle can be separated into two phases: the stance phase (0 to 60%) in which the foot is in contact with the ground, and the swing phase (60% to 100%) in which the heel is in the air.

This term defines all the gait styles and running styles; for example, marching on the spot must be regarded as part of the category defined by the term 'gait cycle'.

The device 1 illustrated in FIG. 1a comprises measurement sensors 2 for measuring raw signals i of a physical variable of a body segment, measured in a sequence of N gait or running cycles of at least one of the individual's feet.

The measurement sensors 2 may be any sensor, such as, for example: an accelerometer, a gyroscope, electromyography, insole pressure sensors or infra-red trackers/video or IR acquisition devices.

They can be placed, for example, on the foot, ankle, waist, wrist or head.

The physical variable measured may be, for example, the magnitude of the acceleration, the magnitude of the non-gravitational acceleration, the speed, the angular velocity, movement, position, etc.

For example, the values emitted by inertial sensors may be linear acceleration or angular velocity along one of the three spatial axes. By means of other sensors, other values can be the position of the foot in space using stereophotogrammetry, or the pressure on the ground using force-sensitive insoles having pressure sensors.

As shown in FIG. 1a, the device 1 comprises a processing and calculation unit 3 set up to:
  process and separate the raw data into distinct time signals $C_i$, each time signal $C_i$ being a series of points of the physical variable measured as a function of time and having a given shape, amplitude and duration, the series $C_i$ being associated with a given single cycle i of the person among the N gait cycles as shown in FIG. 2;
  calculate at least one similarity coefficient between a signal $C_i$ associated with a cycle i and another signal $C_j$ associated with another cycle j, representing the similarity between the two signals $C_i$ and $C_j$;
  order the value of the similarity coefficient between cycles i and j in a square matrix $M(i,j)$, indexed in row i and in column j, and indicating it for each cell $(i,j)$.

In these calculations and when ordering the determined values in the matrix $M(i,j)$, the natural integers for i and j range from 1 to N, and the N gait cycles investigated are in chronological order, for the given foot, according to their order in the gait sequence.

Thus for example,
  cycle 1 is compared with cycle 2 (m[1,2] or m[2,1]), cycle 3 (m[1,3] or m[3,1]), cycle 4 (m[1,4] or m[4,1]), etc.
  cycle 2 is compared with cycle 1 (m[2,1] or m[1,2]), cycle 3 (m[3,1] or m[1,3]), cycle 4 (m[2,4] or m[4,2]), etc.
  and so on.

By design, the matrix also shows the case in which cycle 1 (m[1,1]), cycle 2, etc. are compared with themselves.

Figures 10A, 10B, 10C:
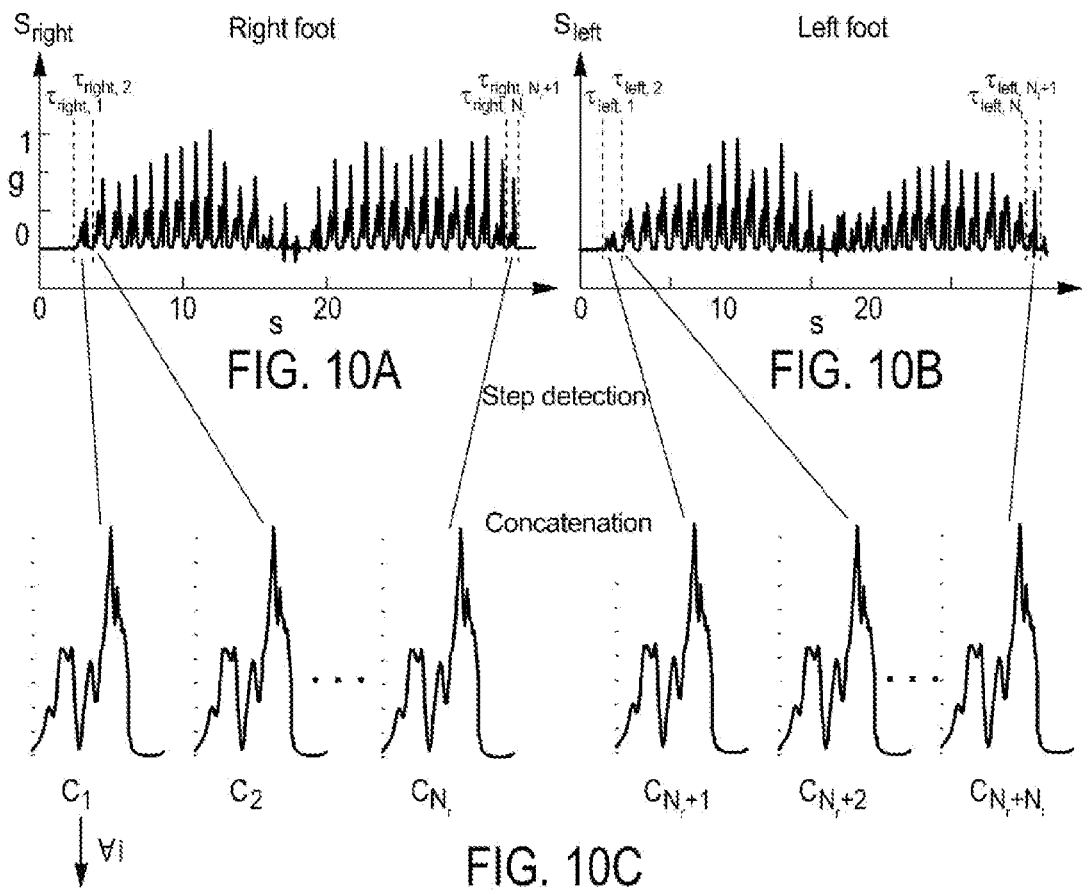
FIGS. 10a and 10b show, as a function of time, the magnitude of the non-gravitational acceleration of the right foot of the person, the magnitude of the non-gravitational acceleration of the left foot of the person and the tracking of the times i_right and i_left corresponding to the gait cycles C1, C2 ... Cnr+nl in a given gait exercise involving walking a defined distance 'there and back'.
FIG. 10c shows the concatenation of the gait cycles C1, C2 ... Cnr+nl.
Figure 10D:
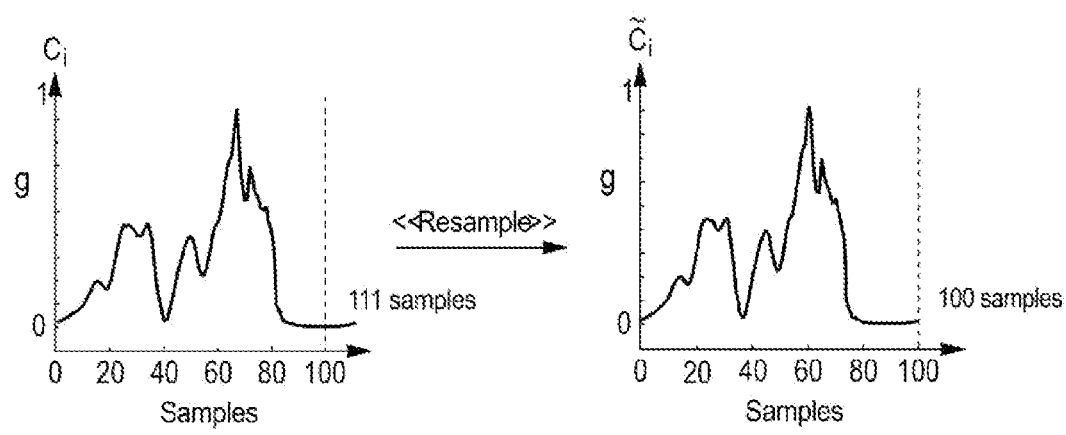
FIG. 10d shows the resampling of the gait cycles C1, C2 ... Cnr+nl.

The processing ('compend resampling') and the separation of the raw data are illustrated in FIGS. 10A to 10D, and the distinct time signals $C_i$ after processing (above) are referred to as $\tilde{C}_i$ in FIG. 10D (which corresponds to the term C'i in the text).

Figures 4A, 4B:
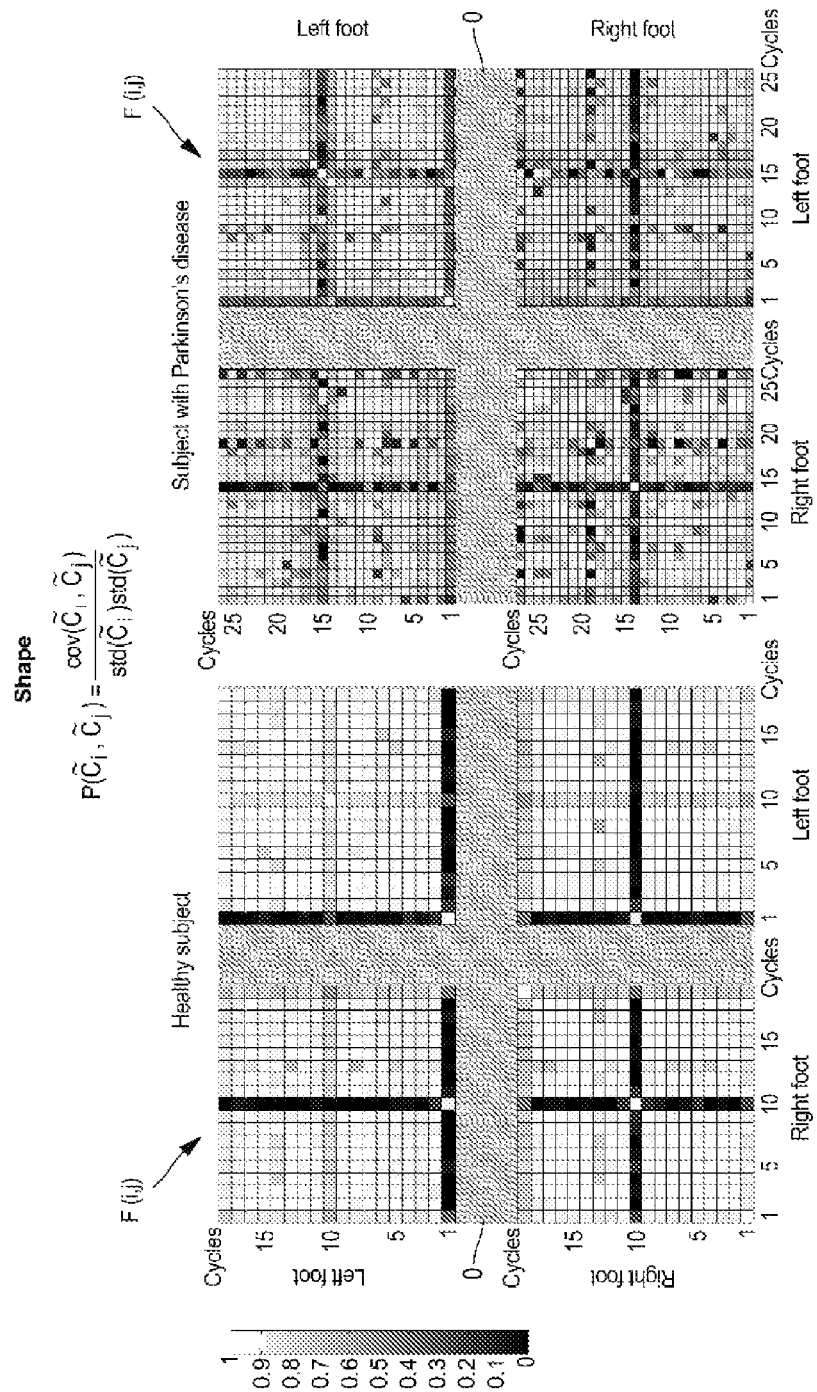
FIGS. 4a and 4b show the visualisation tool F(i,j) which relates to the shape similarity coefficient according to the invention for a healthy subject and for a subject with Parkinson's, respectively, comparing for each subject the shape of their gait cycles in a given gait exercise involving walking a defined distance 'there and back'.
Figures 5A, 5B:
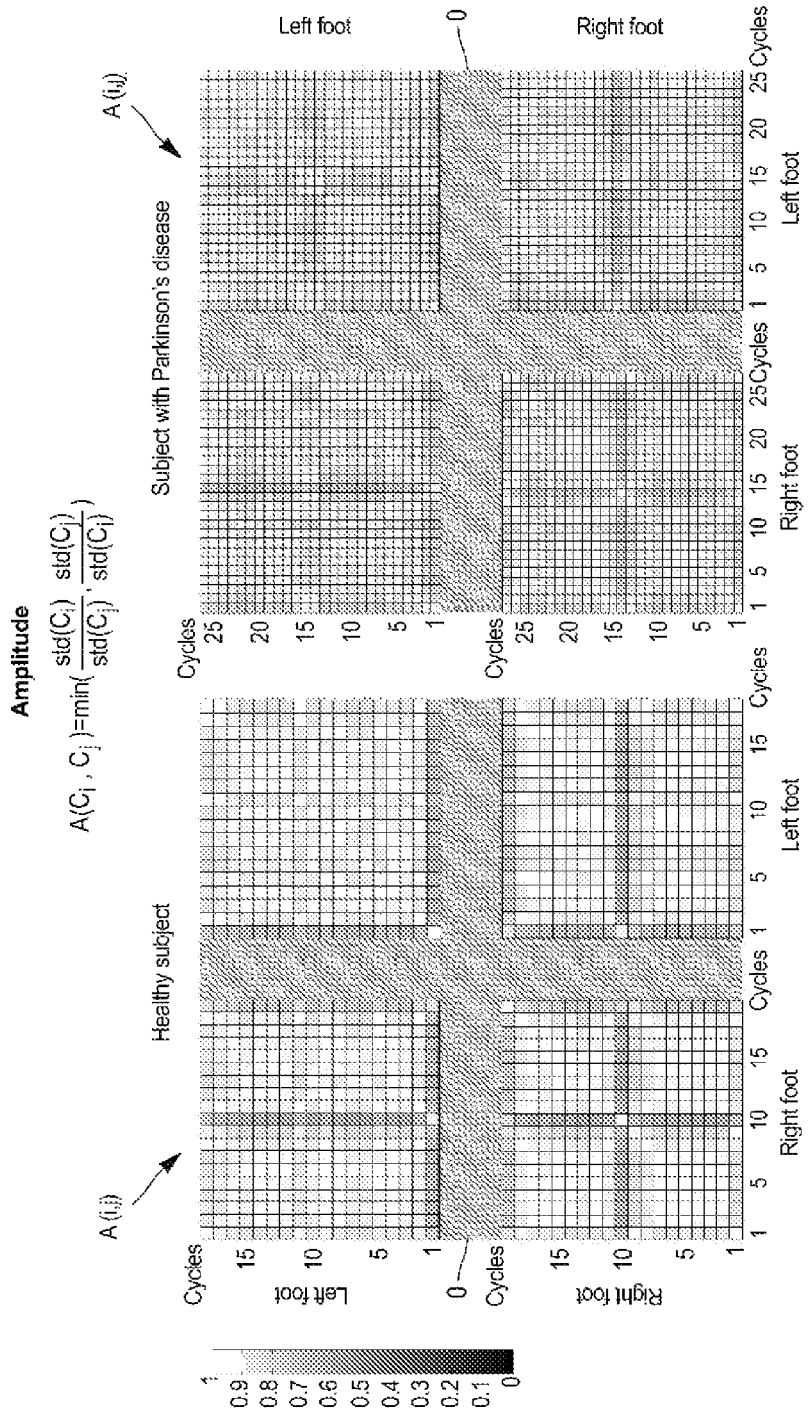
FIGS. 5a and 5b show the gait visualisation tool or square matrix A(i,j) which relates to the amplitude similarity coefficient according to the invention for a healthy subject and for a subject with Parkinson's, respectively, comparing for each subject the amplitude of their gait cycles in a given gait exercise involving walking a defined distance 'there and back'.
Figures 6A, 6B:
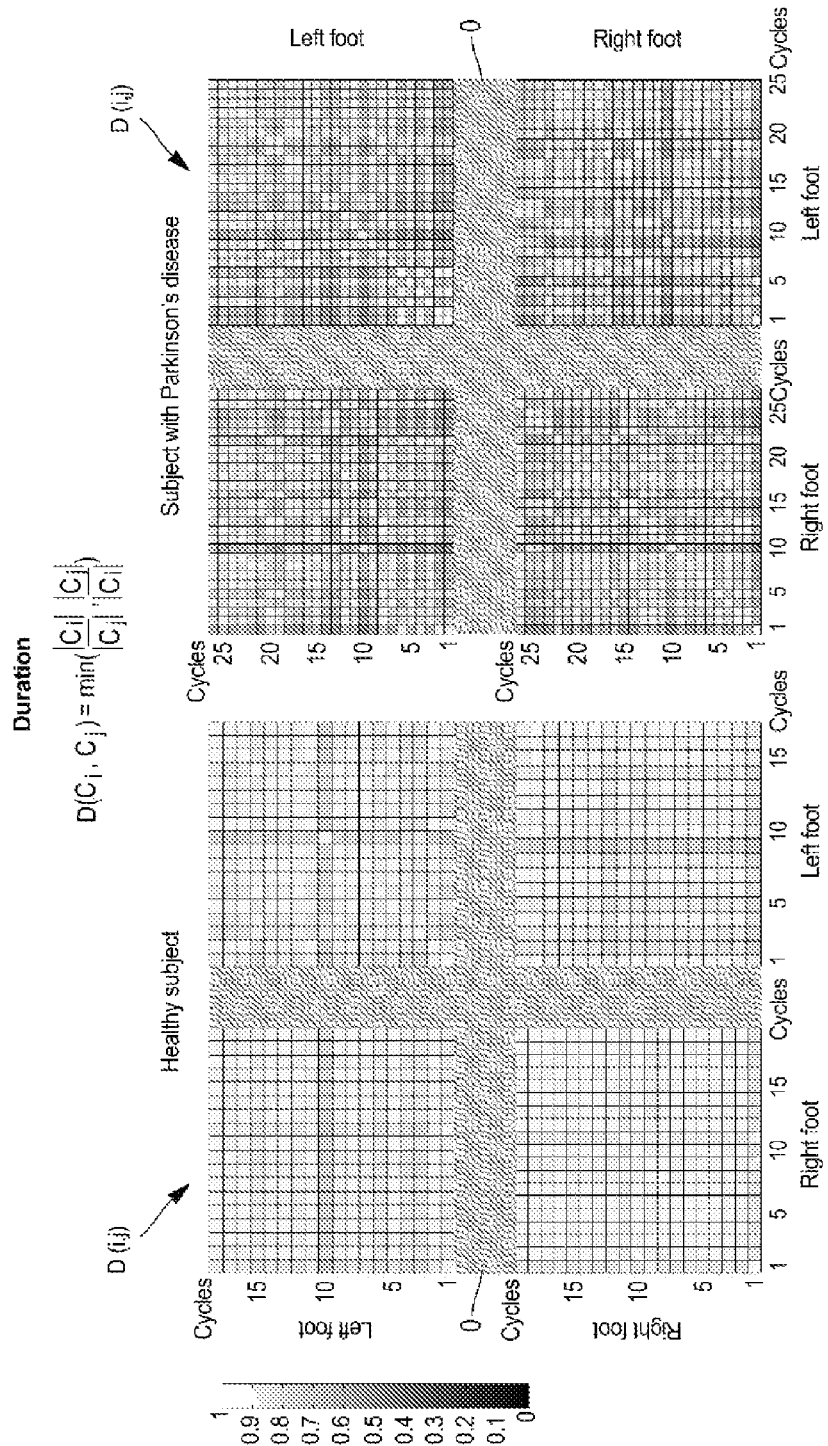
FIGS. 6a and 6b show the gait visualisation tool or square matrix D(i,j) which relates to the duration similarity coefficient according to the invention for a healthy subject and for a subject with Parkinson's, respectively, comparing for each subject the duration of their gait cycles in a given gait exercise involving walking a defined distance 'there and back'.

The similarity coefficient may be: a similarity coefficient of the shape $f_{ij}$ of the two signals $C_i$ and $C_j$ (as represented in FIGS. 4a and 4b), a similarity coefficient of the amplitude $a_{ij}$ of the two signals $C_i$ and $C_j$ (as represented in FIGS. 5a and 5b), or a similarity coefficient of the duration $d_{ij}$ of the two signals $C_i$ and $C_j$ (as represented in FIGS. 6a and 6b).

A synonym of 'coefficient' is 'algebraic distance' in the mathematical sense of the term, for example, and a synonym of 'similarity' is 'resemblance'.

The term 'similarity' implies the symmetry of the coefficients and therefore that $f_{ij}=f_{ji}$, $a_{ij}=a_{ji}$ and $d_{ij}=d_{ji}$.

The similarity coefficient can be regarded as a coefficient of correlation in a certain number of cases in the figures.

Other similarity coefficients can be used depending on the aspect of the shape to be compared between two signals: dynamic time warping (DTW), Spearman's coefficient, Euclidean distances (L1, L2 and L∞).

Thus, with a similarity coefficient which varies within a range [a; b],
  if two signals (or the two gait or running cycles) are identical, the coefficient may be equal to b, and
  if two signals (or the two gait or running cycles) have no resemblance to each other, the coefficient may be equal to a,
  the similarity between the signals increasing linearly between a and b.

Advantageously, the processing and calculation unit 3 is set up to:
  calculate several different similarity coefficients $f_{ij}$, $a_{ij}$ and $d_{ij}$, each similarity coefficient $f_{ij}$, $a_{ij}$ or $d_{ij}$ being associated with the same colour scale, each colour having the same meaning in terms of similarity, whichever similarity coefficient is used, whether $f_{ij}$, $a_{ij}$ or $d_{ij}$, as illustrated in FIGS. 4a to 6b;
  present the values of the similarity coefficients $f_{ij}$, $a_{ij}$, $d_{ij}$ in the different square matrices $[F(i,j), A(i,j), D(i,j)]$, one square matrix per type of similarity coefficient.

The device 1 also has display means 4 linked to the processing unit and displaying the matrix $M(i,j)$ for i and j ranging from 1 to N, each similarity coefficient value being represented in the matrix $M(i,j)$ by a graduated visual representation to make it possible for the similarity between the gait or running cycles i and j to be seen with the naked eye.

Advantageously, the similarity coefficients ($f_{ij}$, $d_{ij}$, $a_{ij}$) are chosen:
  such that once calculated, all the values of the similarity coefficients ($f_{ij}$, $a_{ij}$, $d_{ij}$) are in the same interval [a; b] and
  such that the higher the values of the similarity coefficients ($f_{ij}$, $a_{ij}$, $d_{ij}$), the more similar the signals $C_i$, $C_j$.

Advantageously, this visual representation is graduated to represent the value of the similarity coefficient. In other words, there is a correspondence between the scale of similarity coefficient values and that of the colours.

This correspondence may or may not be proportional.

Preferably, each value is represented by a colour on a graduated colour scale to make it possible for the similarity between the two gait or running cycles i and j to be seen with the naked eye (which amounts to investigating the similarity between the two signals Ci and Cj).

Advantageously, the scale used by the display means 4 is chosen without thresholds or is continuous as illustrated in FIGS. 3 to 6*b*.

Here, the scale is [0, 1] for the shape similarity coefficient, the amplitude similarity coefficient and the duration similarity coefficient, permitting quick and easy comparison of the different similarity coefficients with each other.

Each matrix box can have a colour corresponding to the degree of similarity/resemblance of two steps to each other.

A warm colour (red, for example) is close to 1 and expresses a high degree of resemblance (similarity).

A cool colour (blue, for example) is close to 0 and expresses a low degree of resemblance (similarity).

It should be noted that this scale is inverted between FIG. 3 on the one hand and FIGS. 4*a* to 6*b* on the other: in FIG. 3, dark colours indicate a resemblance, whereas the opposite is the case in FIGS. 4*a* to 6*b*, where light colours indicate a resemblance.

The display means 4 display a visual representation of the matrix of similarity such that:
  each box represents a similarity coefficient between signal Ci and signal Cj;
  the value of the similarity coefficient (fij, aij, dij) is represented in a graduated colour scale.

In a first embodiment illustrated in FIG. 3, the similarity coefficient between the signal Ci relating to the gait or running of one of the person's feet (right or left foot, respectively) and the signal Cj relating to the gait or running of the same foot, and the number of N=Nr (or Nl) cycles, number of cycles of the right foot (or the number of cycles of the left foot) are represented.

In a second embodiment illustrated in FIGS. 4*a* to 6*b*, the display means 4 display:
  the similarity coefficients (fij, aij, dij) calculated for a single foot 3;
  also the similarity coefficient (fij, aij, dij) between the signal Ci relating to the gait or running of the person's right foot and the signal Cj relating to the gait or running of the person's left foot, and N=Nr+Nl.

In this case, all the investigated cycles of the right foot, then all the investigated cycles of the left foot (or vice versa) are in chronological order, on the x and y axis of the matrix, as illustrated in FIGS. 4*a* to 6*b*. They are separated here in the representation by a zone O, which results in four subsquares.

Thus, the similarity matrix:
  'right foot/right foot' is represented by the bottom left subsquare;
  'left foot/left foot' is represented by the top right subsquare;
  'left foot/right foot' is represented by the bottom right subsquare.

When the similarity coefficient is a coefficient of shape fij, the processing and calculation unit 3 is set up to:
  normalise each time signal Ci, in terms of duration, with each time signal Cj so that the two signals Ci and Cj have the same duration;
  normalise each time signal Ci in terms of amplitude;
  calculate a shape similarity coefficient fij between each normalised signal C'i and another normalised signal C'j, for all gait cycles.

In other words, to investigate the resemblance of the shapes of the cycles to each other, their difference in amplitude and their difference in duration need to be eliminated.

For example, the normalisation in terms of duration is performed by linear resampling or by DTW, as illustrated in FIG. 10*c*.

For example, the normalisation in terms of amplitude is performed by dividing the signal Ci by the standard deviation or by the root mean square.

In a first embodiment, the shape similarity coefficient fij may be Pearson's coefficient, as illustrated in FIGS. 4*a* and 4*b*, the values being brought back to 0 if the values of Pearson's coefficient are below zero.

Other mathematical distances are possible, such as Spearman's correlation distance or the dynamic time warping technique.

If only the shape is of interest, it is important to eliminate the amplitude and the duration. To do so, the signal is re-normalised by resampling the signal in 100 samples (normalisation in terms of duration) and dividing the signal by the standard deviation of the cycle (normalisation in terms of amplitude). The Pearson's correlation distance preserves the time line and strictly compares the shape of the steps. Spearman's correlation distance and dynamic time warping deform the time line and indicate whether a deformation is possible to make the shape of two cycles resemble each other or if the shapes are truly different.

In a second embodiment, the similarity coefficient may be a duration similarity coefficient dij.

In this case, as illustrated in FIGS. 5*a* and 5*b*, the processing and calculation unit 3 is set up, for example, to:
  calculate a duration Di, Dj of the signal Ci and of the duration of signal Cj,
  calculate the duration similarity coefficient dij, which is the ratio of the shortest of the two durations Di, Dj to the longest duration Di, Dj, in order to bring the value of the coefficients between 0 and 1.

The duration of the signal Ci is equal to the number of samples, each sample being taken regularly at a given frequency.

In a third embodiment, the similarity coefficient may be an amplitude similarity coefficient.

In this case, as illustrated in FIGS. 6*a* and 6*b*, the processing and calculation unit 3 is set up, for example, to:
  calculate an amplitude Ai, Aj of the signal Ci and of the signal Cj,
  calculate the amplitude similarity coefficient aij, which is the ratio of the smallest amplitude Ai, Aj to the largest amplitude Ai, Aj, in order to bring the value of the coefficients between 0 and 1.

The amplitude Ai and Aj is, for example, the standard deviation or the root mean square.

Once the calculations have been performed to find the values of the similarity coefficients,
  the processing and calculation unit 3 is set up to calculate:
  parameters for evaluating the regularity of the gait;
  parameters for evaluating the symmetry of the gait;
  the number of cycles necessary to establish a gait sequence or sub-sequence.

In particular:
the parameter evaluating the regularity of the gait: the mean of all the cells (i,j) of the matrix M(i,j) [A(i,j), D(i,j), F(i,j)], excluding the cells i=j,
the parameter evaluating the regularity of the gait: the standard deviation of all the cells (i,j) of the matrix M(i,j), excluding the cells i=j,
the parameter evaluating the symmetry of the gait: the mean of the coefficients of the cells, where i ranges from 1 to Nr (or from 1 to Nl), and j ranges from Nr+1 to Nr+Nl (j ranging from Nl+1 to Nr+Nl).

The present invention also concerns a method illustrated in FIG. 2 and using the device 1 described above.

The method, illustrated in FIG. 2, comprises:
a detection step (i) for detecting the raw time signals;
a processing and separation step (ii) for processing and separating the raw time signals into distinct time signals Ci;
a calculation step (iii) for calculating a similarity coefficient;
an ordering step (iv) for ordering the value of the similarity coefficient in a matrix M(i,j) in row i and in column j;
where i and j are natural integers ranging from 1 to N, the N gait or running cycles being in chronological order;
a display step (v) for displaying the matrix M(i,j);
a viewing step (vi) performed by an operator.

The viewing step performed by the operator makes it possible to determine:
the number of cycles necessary to establish a gait or running sequence or gait sub-sequence, the gait or running subsequence being: an about-turn, the start of the walking or running, an acceleration, a deceleration, an established rhythm, the stop, a turn;
the number of cells of a colour associated with a low coefficient value;
whether a cycle has one or more cells of a colour associated with a low or high coefficient value;
whether two consecutive gait cycles have one or more cells of a colour associated with a low or high coefficient value;
to find changes in step rhythm during the exercise by means of colour differences;
to compare the colour of the right foot-right foot cells with the right foot-left foot cells.

The processing and calculation unit 3 can be designed to count the number of cycles defined above, or to display only certain similarity coefficient values among the cycles in the light of predefined threshold values.

Description of the Procedure for Performing a Gait Exercise and Description of the Parkinson's Patient Cohort According to AVC 2

Step 1: Data Acquisition

Figure 7:
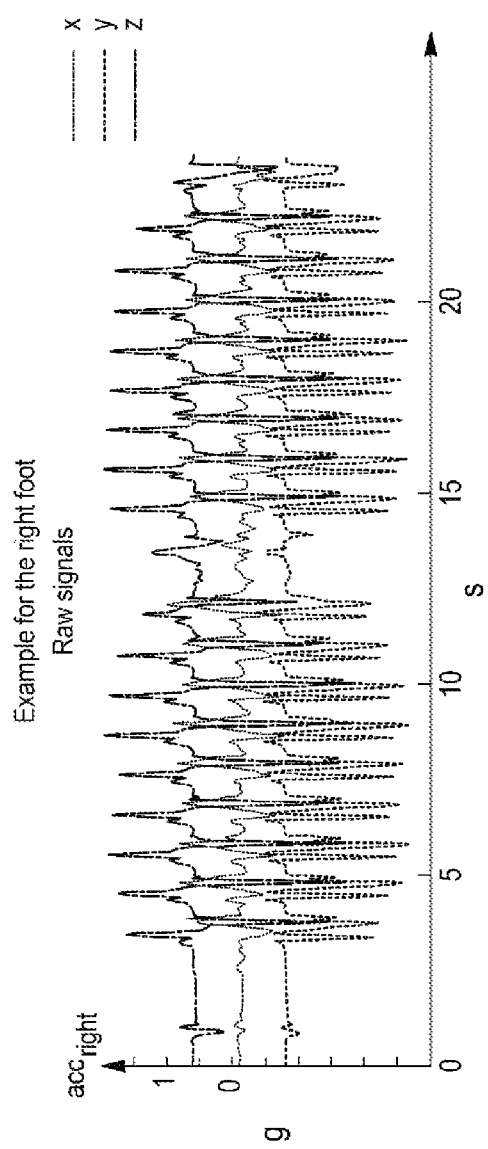
FIG. 7 shows, as a function of time, raw time signals of acceleration emitted by a triaxial accelerometer along the three axes x, y and z for the right foot of a person moving in a given gait exercise involving walking a defined distance 'there and back'.

A subject wearing a triaxial accelerometer on the dorsal surface of each foot performs a walking exercise of 10 metres 'there and back', start-stop. Each of the sensors records a time signal in three dimensions (along the three axes x, y and z). The signals for the right foot and the left foot are called, respectively, $acc_{right}$ and $acc_{left}$, as represented on the curves of FIG. 7.

Step 2: Finding the Beginnings of the Gait Cycles

The times corresponding to the beginnings of the gait cycles are found (manually or automatically) in the signals. These moments, according to the definition by Mariani et al. (2013), correspond to the heel strikes, i.e. the moments when the heel touches the ground. Two $\tau_{right}$ and $\tau_{left}$ sets are defined, which correspond, respectively, to the set of heel strikes for the right foot and the set for the left foot (FIGS. 10A and 10B). The number of heel strikes found for the right foot and the number for the left foot are called $N_r+1$ and $N_l+1$, respectively. The gait cycle i of the right foot is defined as the part of the signal starting at moment $\tau_{right,i}$ and ending at the start of the next gait cycle $\tau_{right,i+1}$, as FIGS. 10A and 10B show. Thus, $N_r$ and $N_l$ are the numbers of gait cycles of the right foot and the left foot, respectively.

Step 3: Removal of Gravity

At the start of the procedure, or in a preliminary step, the subject was asked to remain upright and stationary. The value (constant) of the accelerations during this phase was $$\text{recorded and stored in a vector} \begin{pmatrix} accstationary_{right,x} \\ accstationary_{right,y} \\ accstationary_{right,z} \end{pmatrix}$$

Figure 8:
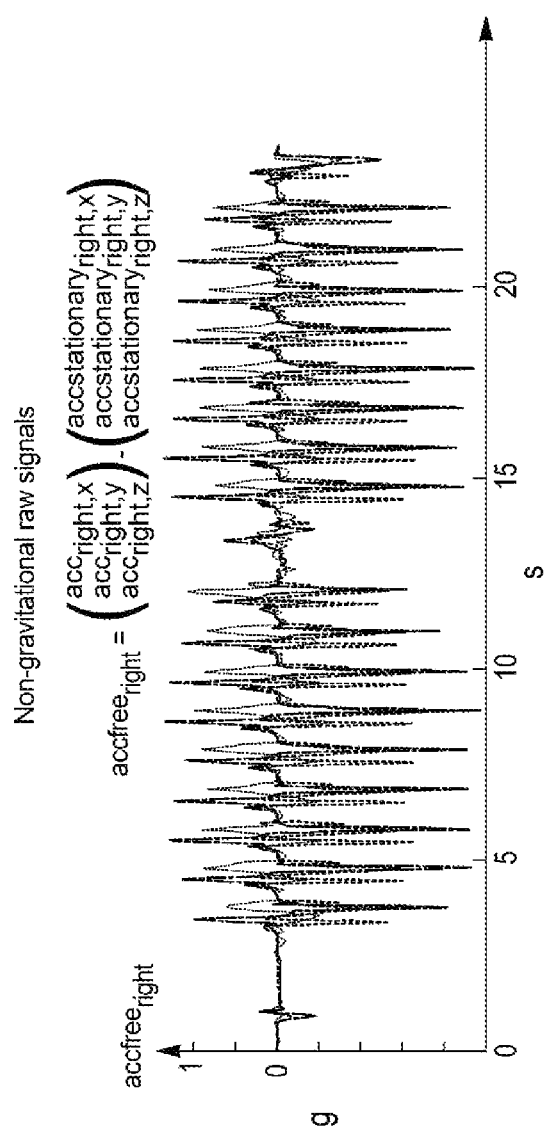
FIG. 8 shows, as a function of time, raw time signals of acceleration without gravity corresponding to the raw signals of FIG. 1 from which the raw time signals emitted by the triaxial accelerometer along the three axes x, y and z for the right foot of a stationary person have been subtracted.

As shown on the curves of FIG. 8, gravity is eliminated by the following procedure:

$$accfree_{right} = \begin{pmatrix} acc_{right,x} \\ acc_{right,y} \\ acc_{right,z} \end{pmatrix} - \begin{pmatrix} accstationary_{right,x} \\ accstationary_{right,y} \\ accstationary_{right,z} \end{pmatrix}$$

The same procedure is repeated for the left foot.

Step 4: Calculation of the Magnitude

Figure 9:
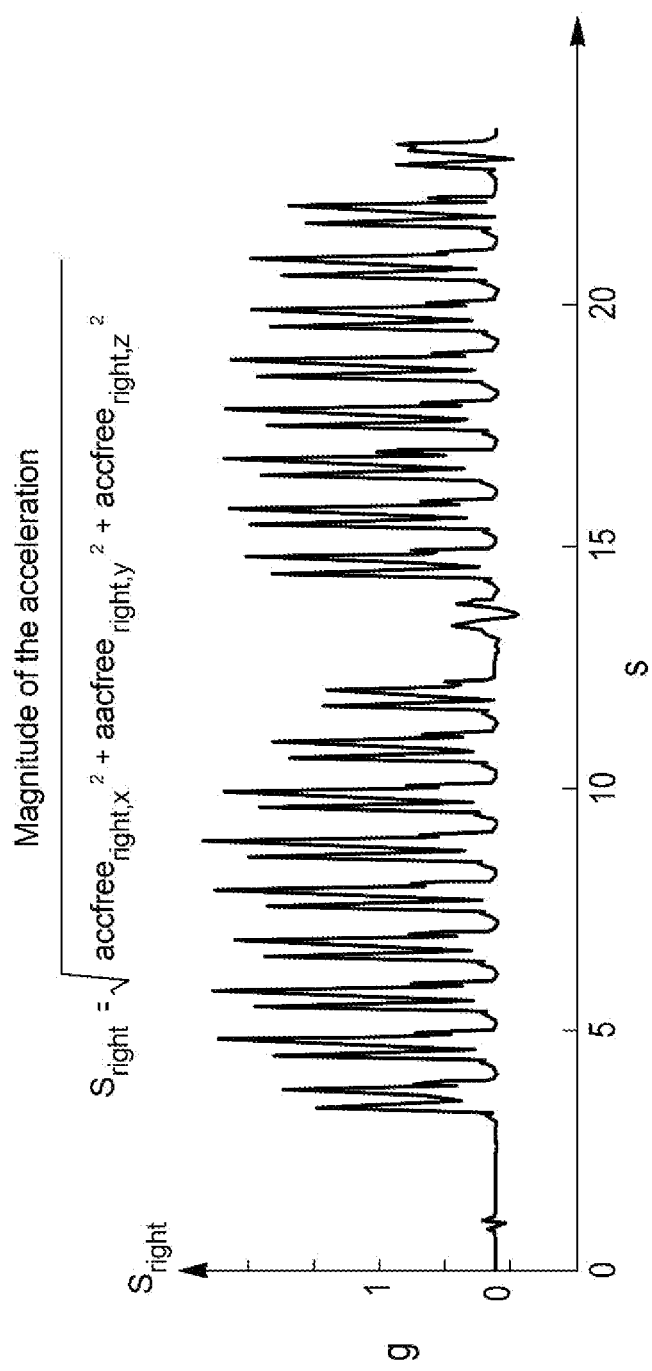
FIG. 9 shows, as a function of time, the magnitude of the non-gravitational acceleration of the right foot of the person in a given gait exercise involving walking a defined distance 'there and back'.

As shown on the curve of FIG. 9, the magnitude of the acceleration vector is calculated at each moment t:

$$s_{right}[t] = \sqrt{accfree_{right,x}[t]^2 + accfree_{right,y}[t]^2 + accfree_{right,z}[t]^2}$$

and in the same way for the left foot.

This fusion of the three axes of acceleration allows or independence in the position of the sensor, which is a major source of measurement imprecision in measurements by accelerometer.

Step 5: Creation of the Gait Cycles

As shown on the curve of FIGS. 10C to 10D, the set of gait cycles of the exercise is recorded in the following way:

For $$\forall i \in [[1, N_r + N_l]] \begin{cases} c_i = s_{right}[\tau_{right,i}, \tau_{right,i+1}] & \text{if } 1 \leq i \leq N_r \\ c_i = s_{left}[\tau_{left,i-N_r}, \tau_{left,i-N_r+1}] & \text{if } N_r + 1 \leq i \leq N_r + N_l \end{cases}$$

$\{c_1, c_2, \ldots, c_{N_r}, c_{N_r+1}, c_{N_r+2}, \ldots, c_{N_r+N_l}\}$, the set of gait cycles of a gait exercise is obtained using $\{c_1, c_1, \ldots, c_{N_r}\}$ the right-foot cycles and $\{c_{N_r+1}, c_{N_r+2}, \ldots, c_{N_r+N_l}\}$ the left-foot cycles.

Step 6: Calculation of the Metrics

From all these steps, a time signal Ci is determined, comprising a series of points of the physical variable measured as a function of time.

Each time signal Ci has a given shape, amplitude and duration, the series Ci being associated with a given cycle i, as represented in FIG. 2.

6.1 Some Preliminary Notes

Given a vector x made up of N samples $\{x_1, x_2, \ldots, x_N\}$, the following quantities are defined:

$$\text{Mean: } \bar{x} = \frac{1}{N}\sum_{i=1}^{N} x_i$$

$$\text{Standard deviation: } std(x) = \frac{1}{N}\sum_{i=1}^{N}(x_i - \bar{x})^2$$

Given two vectors x and y, the following is defined:

$$\text{Covariance: } cov(x, y) = \frac{1}{N}\sum_{i=1}^{N}(x_i - \bar{x})(y_i - \bar{y})$$

6.2 Duration Metric

The duration metric is defined according to:

$$\forall\ i,\ j \in [[1, N_r + N_l]]^2\ D(c_i, c_j) = \min\left(\frac{|c_i|}{|c_j|}, \frac{|c_j|}{|c_i|}\right)$$

where $|c_j|$ is the number of elements of the cycle j.

This is the ratio of the cycle durations, always using the longest cycle as the denominator.

6.3 Amplitude Metric

The amplitude metric is defined according to:

$$\forall\ i,\ j \in [[1, N_r + N_l]]^2\ A(c_i, c_j) = \min\left(\frac{std(c_i)}{std(c_j)}, \frac{std(c_j)}{std(c_i)}\right)$$

This is the ratio of the standard deviations, always using the largest amplitude as the denominator.

6.4 Shape Metric

At this stage, the cycles do not all have the same length. The length of each cycle is normalised to 100 samples using the 'resample' function of Matlab® ('MATLAB 2014a, The MathWorks, Natick, 2014.'), as shown in FIGS. 10D. $\tilde{c}_i$ is referred to as the normalised version of $c_i$ Finally, the shape metric is defined according to:

$$S(c_i, c_j) = \max(0, P(\tilde{c}_i, \tilde{c}_j))$$

Where $$\forall\ i,\ j \in [[1, N_r + N_l]]^2\ P(\tilde{c}_i, \tilde{c}_j) = \frac{cov(\tilde{c}_i, \tilde{c}_j)}{std(\tilde{c}_i)std(\tilde{c}_j)}$$

Step 7: Design of the Visualisation Matrices

In this way, three matrices are obtained for one gait exercise $$[D(c_i, c_j)]_{\substack{i=1 \ldots N_r+N_l \\ j=1 \ldots N_r+N_l}} [A(c_i, c_j)]_{\substack{i=1 \ldots N_r+N_l \\ j=1 \ldots N_r+N_l}} [S(c_i, c_j)]_{\substack{i=1 \ldots N_r+N_l \\ j=1 \ldots N_r+N_l}}$$

We have the following form:

$$\begin{bmatrix} \text{Comparison right left} & \text{Comparison left} \\ \text{Comparison right} & \text{Comparison right left} \end{bmatrix}$$

Detailed Description of the Matrices

FIGS. 4A to 6B are described here.

The figures presented in this document are for the purpose of illustration. According to the design of the 'locogram', the size does not differ between shape, amplitude and duration. The differences in number of squares observed here between FIGS. 4A and 6B are due to a page layout error.

The healthy subject did a total of 38 cycles versus 54 for the Parkinson's patient for the same distance, which shows a pathological gait with small steps (FIGS. 4A and 4B). In the shape matrix for the healthy subject, the uniform squares in a light colour show a regular gait (FIG. 4A). An established walking rhythm is observed to be achieved in one cycle, as only cycle 1 of the right foot is very different from the others. For the Parkinson's patient, the heterogeneity of the shape matrix shows an irregular gait (FIG. 4B). The stable rhythm is reached in two cycles (cycle 1 of the left foot and cycle 1 of the right foot).

The patches of uniformity along the diagonal of the 'locogram' are signs of quality walking. In fact, this means that all the cycles in this patch of uniformity resemble each other and are regular.

In FIG. 4A (healthy subject), these patches are long and ubiquitous. Two of them are distinguished for each foot, and they correspond to the walk there and back of the gait exercise. The walk there and the walk back for each foot are separated by a black cycle (central cross in the bottom left and top right squares: cycle 10, right foot, for example), which corresponds to the about-turn cycle and which does not resemble any other cycle, as is normal.

In FIG. 4B (subject with pathology), the patches of uniformity are shorter. Several uniform patches are found: cycles 2 to 6 and cycles 20 to 25 for the right foot, cycles 2 to 7, cycles 10 to 14 and cycles 15 to 26 for the left foot. It should be noted that these patches of uniformity are relative in nature. In fact, they are uniform compared with the rest of the 'locogram' of FIG. 4B, but relatively heterogeneous compared with the 'locogram' of FIG. 4A. In FIG. 4B, these patches are at the start of the walk: the subject is not tired and can achieve quality walking. These patches are also at the end of the exercise, which may be an indication of a considerable time required to obtain an established walking rhythm. In the middle of the exercise, the gait has deteriorated, as attested by the absence of uniform patches.

Moreover, erratic cycles are observed, indicating irregularities that are quite localised in time (freezing, stumbling): cycle 19, right foot, cycles 8 and 9, left foot, for example. Finally, irregularities more spread out in time are also observed, taking the form of heterogeneous patches: cycles 15 to 20, right foot and cycles 15 to 20, left foot, for example. It should be noted that these two heterogeneous patches immediately follow the about-turn. This may indicate difficulty in performing the about-turn and resuming quality walking after it. There are no patches of heterogeneity or erratic cycles to be observed in FIG. 4A.

The about-turns are also indicators of the quality of locomotion. In FIG. 4A (healthy subject), the about-turn involves only one cycle, which is physiological: cycle 10, right foot. In FIG. 4B (subject with pathology), the about-turn involves two cycles: cycle 14, right foot, and cycle 15, left foot. It can be seen that the about-turn in FIG. 4B has an impact on the cycles in its vicinity (cycles 14 to 17, left foot, are darker), whereas no such impact is observed in FIG. 4A.

In the amplitude matrix for the healthy subject, the increase followed by decrease in the similarity of the amplitude of acceleration between the cycles is evidence of the establishment of a cruising speed (FIG. 5A). This increase and this decrease are less visible for the Parkinson's patient (FIG. 5B).

In the duration matrix for the control subject, the lighter overall colour than that of the Parkinson's patient is evidence of greater resemblance between the gait cycles in terms of duration (FIGS. 6A and 6B). The uniformity of the colour is evidence of less variability between the gait cycles in terms of duration.

Numerical Analysis Using the 'Locogram' for 40 Subjects

We calculate the standard deviation (SD) of the duration of the gait cycles (set of gait cycles without the first three cycles, the three cycles before the about-turn, the cycles of the about-turn, the three cycles following the about-turn and the last three cycles of the exercise):

$$P0 = SD|c_i|_{i=established\ gait}$$

where $|c_i|$ is the number of samples of $c_i$.

We calculate the mean of the 'locogram' for the established gait:

$$P1 = \text{mean}[S(c_i, c_j)]_{\substack{i=established\ gait \\ j=established\ gait}}$$

We calculate the standard deviation of the 'locogram' for the established gait:

$$P2 = SD[S(c_i, c_j)]_{\substack{i=established\ gait \\ j=established\ gait}}$$

We calculate the number of hierarchical clusters on the 'locogram' obtained using the same stop rule:

$$P3 = \text{cluster}[S(c_i, c_j)]_{\substack{i=1\ \ldots\ N_r+N_l \\ j=1\ \ldots\ N_r+N_l}}$$

Table 1 shows the results comparing the parameters {P1, P2, P3} for two groups of healthy subjects (young and elderly) and patients suffering from Parkinson's disease.

Table 2 shows the results comparing the parameters {P1, P2, P3} with the clinical severity of the disease in Parkinson's patients (evaluated using the UPDRS III score) and the gait quality (evaluated using the speed of walking and P0).

The results show that the 'locogram' for patients suffering from Parkinson's disease is significantly more varied in colour than that of the elderly and young healthy subjects for the 3 parameters {P1, P2, P3} obtained from the 'locogram' (Table 1).

Furthermore, there is a correlation between the clinical findings (UPDRS III score) and the gait quality assessed by the 'locogram' according to the three parameters {P1, P2, P3} obtained from the 'locogram' (Table 2).

Finally, there is a correlation between the gait quality evaluated using the parameters of the prior art (speed of walking and P0) and the gait quality assessed by the 'locogram' according to the three parameters {P1, P2, P3} (Table 2).

Therefore, for a group of 40 subjects, the 'locogram' makes it possible to numerically (and visually) evaluate the gait quality of a patient suffering from Parkinson's disease.

Advantage of the Matrices

The visualisation matrix displayed in FIGS. 4A and 6B calculated for a 10-metre 'there and back', stop-start walking exercise provides access to the following gait parameters:

Number of cycles necessary to perform the exercise;
Number of cycles necessary for the about-turn;
Number of cycles necessary to start the walk.

The visualisation matrix presents these parameters more intuitively than a list would. Furthermore, for the last two parameters, the definition in the literature is based on thresholds that were fixed experimentally. The benefit of a global representation rather than a representation of one parameter is that the errors resulting from an arbitrary threshold can be avoided.

The shape of the visualisation matrix makes it possible answer the following questions:

Is the gait regular overall?
Has the subject achieved an established walking rhythm? At what point in time?
Are there several different established walking rhythms?
Are there erratic gait cycles (freezing)? At what point in time?

The visualisation matrix makes it possible to get an idea of the progress of the gait exercise, unlike the parameters, which do not have a time value. The visualisation matrix provides access to the concept of walking rhythm, which is a concept for which we do not have investigation tools apart from the chronological tracking of parameters gait cycle after gait cycle.

Every individual has a particular walking style, which gives rise to a wide inter-individual variability of the parameters. This style is indicated in the signals by a very reproducible signature of one gait cycle after the other in healthy subjects. The parameters are not a suitable tool for describing this signature. The visualisation matrix, with an appropriate choice of distance (see 'Description of the invention') compares the shape of the steps and evaluates the resemblance of the signature of one cycles to the other gait cycles. Thus, it evaluates the quality and reproducibility of the gait and eliminates the personal style, as the individual variabilities are cancelled out in the space between two cycles of the same person. The visualisation matrix provides a table of cells with a number between 0 and 1 for each subject. This makes it possible to compare the visualisation matrices with each other in a reliable way.

The visualisation matrix provides access to new gait parameters not seen before, such as:

the number of clusters with the same stop rule: a subject with pathology will have more of them.
the gait variability calculated using the mean and standard deviation of all the squares of the table, keeping or excluding the steps of the about-turns or the start of the walk.

This makes the visualisation matrix a useful tool for measuring the long walk that will show whether a subject uses two different gait rhythms, which is a useful clinical indicator (onset of pain in osteoarthritis or freezing in Parkinson's disease, for example). Walking is a pseudoperiodic activity which is naturally subdivided into cycles modulated by physiological changes in walking rhythm (i.e. starting, about-turn and stopping) or pathological irregularities in the established gait. In a walking exercise, there are different gait cycles, such as the cycle for starting to walk (the first four cycles), the established gait cycles, the cycles of preparing for the about-turn, the about-turn cycle and the cycle for stopping walking. Based on this property, the visualisation matrix makes it possible to represent all the walking time using the same method. This makes the visualisation matrix a suitable tool for representing walking in an outpatient setting, covering all phases of the walk.

The main application of the visualisation matrix is the visualisation of a walking exercise. The visualisation matrix can be used for any step exercise, including the 10-metre 'there and back' exercise described above, the Timed Up and Go test and also the walking treadmill and the ambulatory walk.

The visualisation matrix is suitable for the visualisation of a 10-metre 'there and back', stop-start walking exercise measured by means of the magnitude of acceleration of an accelerometer placed on the dorsal surface of the foot, by comparing the gait cycles using Pearson's correlation distance. This procedure is suitable for a routine clinical consultation and permits a summarised representation for direct viewing in the clinical setting.

TABLE 1

Inter-group comparison of P1, P2 and P3 for YC, EC and PD.

| Parameters | | YC | EC | PD | |
|---|---|---|---|---|---|
| P1 | Mean | 0.96 | 0.94 | 0.88 | I-III |
| | SD | 0.02 | 0.04 | 0.05 | II-III |
| P2 | Mean | 0.03 | 0.04 | 0.09 | I-III |
| | SD | 0.02 | 0.04 | 0.07 | II-III |
| P3 | Mean | 5.09 | 5.08 | 6.71 | I-III |
| | SD | 2.30 | 2.59 | 2.72 | II-III |

Statistical test: ANOVA (analysis of variance).
II-III = p value <0.05.
SD: standard deviation
YC (young controls): group of young adults (N = 9, mean age = 38.3 years, SD 8.2 years)
EC (elderly controls): group of elderly adults (N = 11, mean age = 67.0 years, SD 10.1 years)
PD (Parkinson's disease): group of patients suffering from Parkinson's disease (N = 20, mean age = 74.7 years, SD 11.0 years)
P1: parameter mean of the locogram for the established gait (no unit)
P2: parameter standard deviation of the locogram for the established gait (no unit)
P3: parameter number of hierarchical clusters in the locogram obtained using the same stop rule (no unit)

TABLE 2

PD in-group correlation between {P1, P2, P3} and {UPDRS III, speed of walking, P0}

| Parameter | | UPDRS III | Speed of walking | P0 |
|---|---|---|---|---|
| P1 | Rho | −0.51* | 0.67* | 0.30* |
| | Pval | 0.00 | 0.00 | 0.00 |
| P2 | Rho | 0.39* | −0.44* | −0.16 |
| | Pval | 0.00 | 0.00 | 0.06 |

TABLE 2-continued

PD in-group correlation between {P1, P2, P3} and {UPDRS III, speed of walking, P0}

| Parameter | | UPDRS III | Speed of walking | P0 |
|---|---|---|---|---|
| P3 | Rho | 0.23* | −0.47* | −0.27* |
| | Pval | 0.00 | 0.00 | 0.00 |

Correlations evaluated using Pearson's coefficient.
*= p value <0.05.
Rho: coefficient of correlation
UPDRS III: clinical score enabling the neurologist to quantify the severity of the motor skills deficiency in the Parkinson's disease during the consultation.
PD (Parkinson's disease): group of patients suffering from Parkinson's disease
P0: parameter standard deviation of the duration of the gait cycles in the established gait
P1: parameter mean of the locogram for the established gait
P2: parameter standard deviation of the locogram for the established gait
P3: parameter number of hierarchical clusters in the locogram obtained using the same stop rule

The invention claimed is:

1. A method for providing, by a visual representation:
a temporal analysis of a regularity and symmetry of a sequence of N gait or running cycles of the same a person, by comparing each cycle taken individually with each of the other cycles taken individually,
and a determination of a presence and number of erratic cycles as well as a number of cycles necessary to establish gait or running rhythms, and at what point these erratic gait cycles and rhythms are reached, the method comprising the following steps:
a measurement step (i) for measuring raw time signals using sensors that relate to a physical movement variable measured of at least one body segment of the person, where the physical variable measured is chosen from the following list: magnitude of acceleration, magnitude of non-gravitational acceleration, speed, angular velocity, movement, position, or a force exerted by the person when moving on a device,
a processing and calculation step, subdivided into:
a processing and separation step (ii) for processing and separating the raw time signals into distinct time signals $C_i$ in order to break down the gait or run into gait or running cycles, each time signal $C_i$ being a temporal series of points of the measured physical variable and having a given shape, amplitude and duration, the series $C_i$ being associated with a given cycle i of the person's gait or run;
a calculation step (iii) for calculating at least one similarity coefficient between the signal $C_i$ associated with the gait or running cycle i and another signal $C_j$ associated with a gait or running cycle j of the person, the similarity coefficient being at least one of:
a similarity coefficient of a shape $f_{ij}$ of the two signals $C_i$ and $C_j$, which is independent of the amplitude and of the duration, where $f_{ij}=f_{ji}$, or
a similarity coefficient of an amplitude $a_{ij}$ of the two signals $C_i$ and $C_j$, which is independent of the shape and of the duration, where $a_{ij}=a_{ji}$, or
a similarity coefficient of a duration $d_{ij}$ of the two signals $C_i$ and $C_j$, which is independent of the shape and of the duration, where $d_{ij}=d_{ji}$,
an ordering step (iv) for ordering the similarity coefficient in a square matrix $M(i,j)$ in row i and in column j, where i and j are natural integers ranging from 1 to N, the N gait or running cycles being in chronological order, according to their order in the gait or running sequence;

a display step (v) for displaying the square matrix M(i,j) with similarity coefficient values fij, aij or dij shown in cells (ij) of the square matrix M(i,j) using a visual representation of the similarity coefficient value within an interval between two extreme values, continuously without thresholds, to enable determining:

the similarity between all the gait and running cycles i and j of the person, by comparing each cycle taken individually with each of the other cycles taken individually, and the number of erratic cycles and the number of cycles necessary to establish gait or running rhythms, and at what point in the sequence these erratic cycles and rhythms are reached.

2. The method according to claim 1, wherein the processing and calculation step, the similarity coefficient between the signal Ci relating to the gait or running of one foot of the person and the signal Cj relating to the gait or running of the other foot is determined and in that the number of cycles–N=Nf, which is the number of cycles of the foot.

3. The method according to claim 2, wherein in the processing and calculation step, the similarity coefficient between the signal Ci relating to the gait or running of the person's right foot and the signal Cj relating to the gait or running of the same person's left foot is determined, and the number of cycles N is equal to the sum of the number of cycles of the right foot and the number of cycles of the left foot: N=Nr+Nl, Nr and Nl which are the number of cycles of the right foot and the number of cycles of the left foot.

4. The method according to claim 1, wherein the gait or running rhythms determined are: one or more established rhythms, the start of the gait or running sequence, or about-turn.

5. The method according to claim 1, wherein, in the display step (v), each value of the similarity coefficient is represented by a color on a continuous graduated scale corresponding to a scale of similarity coefficients.

6. The method according to claim 5, wherein:
in the processing and calculation step, the three similarity coefficients fij, aij and dij are calculated, each similarity coefficient being associated with the same color scale as the other similarity coefficients, each color having the same meaning in terms of similarity;
in the display step (v), the values of the similarity coefficients are presented in different square matrices [F(i, j), A(i,j), D(i,j)];
the similarity coefficients being chosen:
such that once calculated, all the values of the similarity coefficients fij, aij, dij are in the same interval [a; b] and
such that the higher the values of the similarity coefficients fij, aij, dij, the more similar the signals Ci, Cj are.

7. The method according to claim 1, wherein the similarity coefficient is a shape coefficient, and in the processing and calculation stage:
each time signal Ci is normalized in terms of duration with each time signal Cj so that the two signals Ci and Cj have the same duration;
each time signal Ci is normalized in terms of amplitude;
a shape similarity coefficient fij is-calculated between each normalized signal C'i and another normalized signal C'j, for all gait or running cycles.

8. The method according to claim 7, wherein the shape similarity coefficient is Pearson's coefficient, the values of the similarity coefficient being set to 0 if the value of Pearson's coefficient is below zero.

9. The method according to claim 1, wherein:
the similarity coefficient is a duration similarity coefficient,
a processing and calculation unit (3) is set up to:
calculate a duration Di of the signal Ci and a duration Dj of signal Cj,
calculate the duration similarity coefficient dij, which is the ratio of the shortest of the two durations Di and Dj to the longest of the two durations Di and Dj.

10. The method according to claim 1, wherein the similarity coefficient is an amplitude similarity coefficient,
and a processing and calculation unit (3) is set up to:
calculate an amplitude Ai of the signal Ci and an amplitude Aj of the signal Cj,
calculate the amplitude similarity coefficient aij, which is the ratio of the smallest of the two amplitudes Ai and Aj to the largest of the two amplitudes Ai and Aj.

11. The method according to claim 10, wherein the amplitude Ai, Aj is a standard deviation or a root mean square.

12. The method according to claim 1, further comprising:
calculating parameters for evaluating the regularity of the gait or run;
calculating parameters for evaluating the symmetry of the gait or run;
calculating the number of cycles necessary for a gait or running sequence or sub-sequence.

13. The method according to claim 12, wherein the following are calculated to determine the regularity of the gait or run:
a mean of all cells (i,j) of the square matrix M(i,j), excluding cells i=j,
a standard deviation of all cells (i,j) of the square matrix M(i,j), excluding cells i=j,
a mean of cells i ranging from 1 to Nf, and the cells j ranging from Nf+1 to Nr+Nl.

14. The method according to claim 1, wherein the raw time signals are processed and separated automatically or manually prior to the calculation step (iii) prior to the calculation of the similarity coefficient.

15. A device permitting, by means of a visual representation:
temporal analysis of a regularity and symmetry of a sequence of N walking or running cycles of the a person, by comparing each cycle taken individually with each of the other cycles taken individually, and
a determination of a presence and number of erratic cycles as well as a number of cycles necessary to establish gait or running rhythms, and at what point in the sequence these erratic cycles and rhythms are reached, the device (1) comprising:
sensors for measuring raw time signals that relate to a physical movement measured variable of at least one body segment of the person, the physical variable measured is chosen from the following list: magnitude of acceleration, magnitude of non-gravitational acceleration, speed, angular velocity, movement, position, or a force exerted by the person when moving on the device;
a processing and calculation unit (3), connected to the sensors (2) configured to:
process and separate the raw time signals into distinct time signals Ci, each time signal Ci being a temporal series of points of the measured physical variable and having a given shape, amplitude and duration, the series Ci being associated with a given gait or running cycle i of the person;

calculate at least one similarity coefficient between the signal $C_i$ associated with the gait or running cycle i and another signal $C_j$ associated with a gait or running cycle j of the person, the similarity coefficient being at least one of, a similarity coefficient of the shape $f_{ij}$ of the two signals $C_i$ and $C_j$, which is independent of the amplitude and of the duration, where $f_{ij}=f_{ji}$, or a similarity coefficient of the amplitude $a_{ij}$ of the two signals $C_i$ and $C_j$ which is independent of the shape and of the duration, where $a_{ij}=a_{ji}$, or a similarity coefficient of the duration $d_{ij}$ of the two signals $C_i$ and $C_j$ which is independent of the amplitude and of the shape, where $d_{ij}=d_{ji}$, and order the value of the at least one similarity coefficient in a square matrix $M(i,j)$ in row and in column j where i and j are natural integers ranging from 1 to N, the N gait or running cycles being in chronological order, according to their order in the gait or running sequence, and a display (4) connected to the processing and calculation unit (3), displaying the square matrix $M(i,j)$ with similarity coefficient values shown in the cells (ij) of the square matrix $M(i,j)$, by a visual representation of the at least one similarity coefficient value within an interval between two extreme values, continuously without thresholds, to make it possible to simultaneously view:

the similarity between all the gait and running cycles i and j of the same person, and the presence and number of erratic cycles and the number of cycles necessary to establish gait or running rhythms, and at what point in the sequence these erratic cycles and rhythms are reached.

16. The device according to claim 15, wherein the processing and calculation unit determines the similarity coefficient between the signal $C_i$ relating to the gait or running of one foot of the person, and the signal $C_j$ relating to the gait or running of the foot, and in that $N=N_r$, which is the number of cycles of the foot.

17. The device according to claim 16, wherein the processing and calculation unit determines the similarity coefficient between the signal $C_i$ relating to the gait or running of the person's right foot and the signal $C_j$ relating to the gait or running of the same person's left foot, and the number of cycles N is equal to the sum of the number of cycles of the right foot and the number of cycles of the left foot: $N=N_r+N_l$, $N_r$ and $N_l$ which are the number of cycles of the right foot and the number of cycles of the left foot.

18. The device according to claim 15, wherein the gait or running rhythms determined are: one or more established rhythms, a start of the gait or running sequence, or an about-turn.

19. The device according to claim 15, wherein, in displaying the square matrix, each value of the similarity coefficient is represented by a color on a continuous graduated scale corresponding to a scale of similarity coefficients.

20. The device according to claim 15, wherein the sensors for measuring include: an accelerometer, a gyroscope, an electromyography, an insole pressure sensors, an infra-red kinematic acquisition device or a force platform.

\* \* \* \* \*